United States Patent [19]
Trujillo et al.

[11] 3,933,431
[45] Jan. 20, 1976

[54] METHOD AND APPARATUS FOR SAMPLING ATMOSPHERIC MERCURY

[75] Inventors: Patricio E. Trujillo, Santa Fe; Evan E. Campbell; Bernard C. Eutsler, both of Los Alamos, all of N. Mex.

[73] Assignee: The United States of America as represented by the United States Energy Research and Development Administration, Washington, D.C.

[22] Filed: July 23, 1974

[21] Appl. No.: 491,088

[52] U.S. Cl. ................ 23/232 R; 23/254 R; 55/72; 55/387; 73/421.5 R; 252/444
[51] Int. Cl.² .................... B01D 53/04; B01J 21/18; G01N 1/22; G01N 31/06
[58] Field of Search ......... 55/387, 72, 74, 316, 179, 55/75 US, 76 US; 23/232 R, 254 R; 252/444

[56] References Cited
UNITED STATES PATENTS

| | | | |
|---|---|---|---|
| 3,022,141 | 2/1962 | Grosskopf | 23/254 R |
| 3,193,987 | 7/1965 | Manes et al. | 55/72 |
| 3,232,033 | 2/1966 | Williston et al. | 55/387 |
| 3,257,776 | 6/1966 | Park et al. | 55/72 |
| 3,374,608 | 3/1968 | Manes | 55/72 |
| 3,711,248 | 1/1973 | Coffey | 23/230 R |
| 3,826,618 | 7/1974 | Capuano | 23/232 R |
| 3,844,719 | 10/1974 | Hammitt | 23/254 R X |

Primary Examiner—Joseph Scovronek
Attorney, Agent, or Firm—Dean E. Carlson; Edward C. Walterscheid

[57] ABSTRACT

A method of simultaneously sampling particulate mercury, organic mercurial vapors, and metallic mercury vapor in the working and occupational environment and determining the amount of mercury derived from each such source in the sampled air. A known volume of air is passed through a sampling tube containing a filter for particulate mercury collection, a first adsorber for the selective adsorption of organic mercurial vapors, and a second adsorber for the adsorption of metallic mercury vapor. Carbon black molecular sieves are particularly useful as the selective adsorber for organic mercurial vapors. The amount of mercury adsorbed or collected in each section of the sampling tube is readily quantitatively determined by flameless atomic absorption spectrophotometry.

6 Claims, 4 Drawing Figures

METHOD AND APPARATUS FOR SAMPLING ATMOSPHERIC MERCURY

BACKGROUND OF THE INVENTION

The invention described herein was made in the course of, or under, a contract with the U.S. ATOMIC ENERGY COMMISSION. It relates to apparatus and materials for simultaneously sampling atmospheric metallic mercury vapor and atmospheric organic mercurials and a method for determining the amount of mercury vapor and the amount of organic mercurials in the air volume sampled.

Mercury is used for a wide variety of industrial and chemical purposes. Unfortunately, mercury and its compounds have only recently been generally appreciated as a virulent poison that is readily absorbed through the respiratory tract, the gastrointestinal tract, or through unbroken skin. It acts as a cumulative poison since only small amounts can be eliminated at a time by the human body. The maximum allowable concentration of metallic mercury vapor in air has been set at 0.1 mg/m$^3$ by National Institute of Occupational Safety and Health (NIOSH) for occupational exposure. Since mercury is very volatile, dangerous levels are readily attained in air. Air saturated with mercury vapor at 20°C contains a concentration which exceeds the toxic limit by more than 100 times, and the danger increases at higher temperatures.

Organic mercurials, such as, e.g., $(CH_3)_2Hg$ and $CH_3HgCl$, in the atmosphere present a substantially greater danger than even metallic mercury vapor, because they are absorbed into the bodies of most living creatures at a much faster rate than is mercury vapor. Further, there is little or no tendency of the body to eliminate some of them.

Because many of the organic compounds of mercury are more hazardous than metallic mercury, it is highly useful to know the form of the mercury present in a mercury contaminated environment. One of the major problems encountered in analyzing mercury in air is that of distinguishing contamination from metallic mercury vapor from that of other forms of mercury. In most analytical methods for mercury in air, metallic, particulate, and organic mercury are collected simultaneously and measured as total mercury. Methods for metallic mercury are usually based on amalgamation with precious metals and are not capable of detecting most organic mercurials. Conversely, the metallic mercury methods are often nonspecific for metallic mercury with interferences from particulate mercury and some organic mercurials.

Accordingly, it is readily apparent that a straightforward accurate method of sampling and measuring the content of both metallic mercury vapor and organic mercurials in the occupational environment would be quite advantageous. Further, to be most useful, the method should be capable of sampling mercury vapor and organic mercurials simultaneously but yet be able to distinguish fully between them so that the amount of each in the sampled air is accurately determined. In addition, any such method and its associated apparatus should be capable of accurately sampling low concentrations of mercury vapor and organic mercurials over long periods of time at relatively low flow rates. Finally, the sampling apparatus should be compact enough to be carried or worn in the working environment for long periods without unduly hampering normal work activity.

In U.S. Pat. application Ser. No. 386,465 for "Mercury Sampling Material and Method" filed Aug. 7, 1973, now U.S. Pat. No. 3,888,124, issued June 10, 1975, the present inventors disclose adsorbing media for sampling metallic mercury vapor from an air stream which comprise silver metal coated on finely divided particulate siliceous substrates. Such substrates may range from common sea sand to calcined diatomaceous earths. Particularly useful for the purpose is the calcined diatomaceous earth manufactured and sold under the tradename of Chromosorb P. The amount of mercury adsorbed on the silvered substrate is readily quantitatively determined by flameless atomic absorption spectrophotometry. Heating the silvered substrate to 700°C volatilizes all absorbed mercury and renders the substrate once again useful for mercury vapor sampling.

It is known in the art that iodized charcoals or charcoals prepared from coconut shells are capable of quantitatively adsorbing rather large quantities of mercury vapor and/or organic mercurials. Unfortunately, the charcoals do not differentiate between mercury vapor and organic mercurials, but readily adsorb both simultaneously. In addition, they are highly unsuitable for flameless atomic absorption spectroscopy in that when heated sufficiently to drive off the adsorbed mercury they also tend to produce decomposition products which interfere strongly with the usual spectroscopy methods employed to determine mercury.

SUMMARY OF THE INVENTION

Through use of the apparatus, material, and method of the invention, the content of mercury in air may be quantitatively sampled and the amount present as particulates, organic mercurial vapor, or metallic mercury vapor accurately determined.

The invention encompasses a sampling tube for simultaneously and selectively sampling organic mercurial and metallic mercury vapors from air which comprises (a) a cylinder having an air intake end and an air outlet end, (b) a first particulate adsorber within said cylinder and adjacent said air intake end for selectively and quantitatively adsorbing organic mercurial vapors in air passing therethrough, (c) a second particulate adsorber within said cylinder for adsorbing metallic mercury in air passing therethrough, and (d) porous plug means for maintaining said first and second adsorbers separate from each other in said cylinder, said plug means producing no substantial pressure drop in air passing through said cylinder. The invention also encompasses a method for determining the content of mercury in organic mercurial and metallic mercury vapors in air which comprises (a) passing a known volume of said air through a first adsorber which selectively and quantitatively adsorbs organic mercurial vapors, (b) then passing said air volume through a second adsorber which quantitatively adsorbs mercury vapor, (c) individually thermally desorbing collected vapors from said first and second adsorbers, (d) reducing said desorbed organic mercurial vapors to metallic mercury vapor, and (e) individually measuring by flameless atomic adsorption spectroscopy the amount of metallic mercury vapor obtained from each of said first and second adsorbers. In one embodiment of a sampling tube of the invention, a first adsorber is disposed within a glass tube to selectively and quantitatively adsorb organic mercurial vapors from air passing therethrough while disposed downstream of said first adsorber is a second adsorber which quantitatively adsorbs metallic mercury vapor. The first adsorber for organic mercurial vapors is a large surface area carbon black which preferably can act as a molecular sieve. A preferred material for use as this adsorber is a carbon black prepared by the thermal degradation of polyvinylidene chloride and having a surface area of about 1000 m²/g and a pore radius of 10 to 12 angstroms. The second adsorber, for adsorbing metallic mercury vapors, is a silvered particulate substrate. Silvered siliceous particulates are suitable for this purpose but silvered calcined diatomaceous earths are preferred.

In another embodiment of the invention a filter is attached to the intake end of the sampling tube whereby particulate mercury as well as organic mercurial and metallic mercury vapors may be collected simultaneously for analysis.

The sampling tubes of these embodiments are adapted for use with standard battery operated portable air sampling pumps. They may readily be worn on the upper portion of the body for sampling the occupational and working environment.

When the desired volume of air has passed through the sampling tube, the content of mercury in the air as metallic mercury vapor or as organic mercurial vapors is readily determined in the following manner. The glass sampling tube is broken between the first adsorber and second adsorber sections to form two sections. One section is placed in a thermal desorption unit and heated to 700°C to thermally desorb all mercury. The thermal desorption unit is designed to reduce organic mercurials on the first section to elementary mercury and metallic mercury vapor desorbed is drawn through a flameless atomic absorption spectrophotometer operating on the 2537 A wavelength of mercury where the amount of mercury desorbed from the adsorber in the sampling tube section is measured. The second section of sampling tube containing the other adsorber section is then inserted in the thermal desorption unit and the process is repeated. In the event that particulate mercury is also sampled and analysis required, the filter is removed from the sampling tube and digested with nitric acid. Particulate mercury on the digested filter is reduced to metallic mercury vapor by a chemical process and is transferred into a sampling tube containing a silver-coated particulate substrate. The mercury is then desorbed and measured using the same thermal desorption unit and spectrophotometer as used for the determination of the mercury collected as organic mercurial and metallic mercury vapors.

The mercury contents of each absorption section in the range of 0.3 mg to 3µg are readily analyzed using the method, apparatus, and material of the invention.

DESCRIPTION OF THE PREFERRED EMBODIMENT

Figure 1:
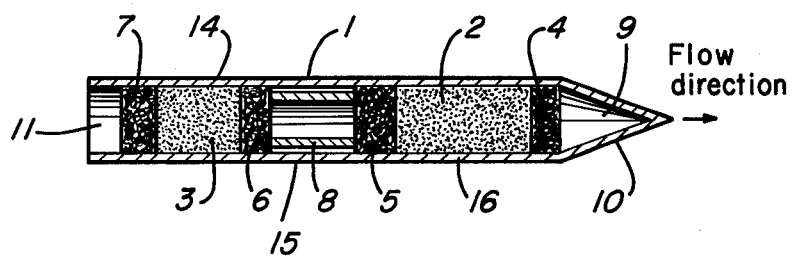
FIG. 1 is a cross-sectional view of a mercury sampling tube in one embodiment of the invention.
Figure 2:
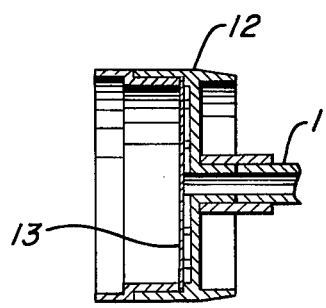
FIG. 2 is a cross-sectional view of a particulate mercury filter which together with the sampling tube of FIG. 1 constitutes a second embodiment of the invention.

An embodiment of a sampling tube useful for sampling organic mercurial vapors, mercury vapor, and particulate mercury in the working and occupational environment is shown in FIGS. 1 and 2. The sampling tube may be either two-stage as shown in FIG. 1 or three-stage with attachment of the particulate mercury filter shown in FIG. 2. The two-stage sampling tube comprises a cylinder or tube 1 containing a material 2 for amalgamating mercury vapor and a material 3 for adsorbing organic mercurial vapors. Materials 2 and 3 are particulate in nature and are held in place by porous plugs 4, 5, 6, and 7. A spacer 8 may be inserted between plugs 5 and 6. Prior to use in the two-stage configuration, tube 1 may be open at both ends or alternatively, as shown in FIG. 1, have its downstream end 9 sealed. In the embodiment shown in FIG. 1 when sampling is to be commenced, seal 10 is broken and removed and the sampling tube is attached to an appropriate pump (not shown). Air to be sampled enters tube 1 through intake 11. In the three-stage configuration, a filter holder 12 for a particulate filter 13 is attached to tube 1 at intake 11 with a tight seal as shown in FIG. 2.

In the embodiment shown in FIG. 1, tube 1 is typically glass or Pyrex tubing flame sealed at one end. Plugs 4, 5, 6, and 7 may be any porous material which will not interfere with mercury absorption and determination or produce any substantial pressure drop in tube 1 and which will hold materials 2 and 3 in place without leakage at 700°C. Quartz glass wool is suitable for this purpose. Spacer 8 is not essential but serves the desirable purpose of maintaining a central section 15 of tube 1 free of any adsorber and aiding in the separation of the absorber sections. After sampling has occurred tube 1 can then be readily broken in two at this section before analysis of the amalgamating material 2 or adsorber 3. This avoids any possibility of contamination of one adsorber by the other during subsequent processing. Spacer 8 may be of any inert material free of mercury and of any geometry which will maintain plugs 5 and 6 at the desired spacing and permit a free flow of gas therethrough. Typically, it is merely a section of glass tubing having an outside diameter which will fit into tube 1. In the three-stage embodiment of FIG. 2, particulate filter 13 may be any material which will collect particulate mercury but allow passage of organic mercurial and mercury vapors therethrough. Filter holder 12 may be of any geometry that will hold filter 13 securely in place such that any gas entering intake 11 of tube 1 must first pass through filter 13. Suitable filters include common laboratory membrane filters. If such filters are used, they preferably will have a larger diameter than tube 1, as will filter holder 12, so as to alleviate any pressure drop that may be associated with their use.

Amalgamating material 2, which is used to collect mercury vapor quantitatively, is a silvered siliceous particulate. As used within this application, a siliceous material is one which is composed of about 50% or more of silica. A silvered substrate is one which has been coated or plated with a thin layer of silver. Particulate substrates may readily be silvered according to the following technique. A silver nitrate solution is prepared by dissolving 20 g of $AgNO_3$ crystals in 30 cm³ of distilled water. Ammonium hydroxide solution (28%) is stirred into the AgNO₃ solution until a dark brown precipitate of Ag₂O forms and the solution begins to clear. A second AgNO₃ solution, prepared by dissolving 4 g of AgNO₃ crystals in 60 cm³ of distilled water, is then added dropwise until the solution is a distinct straw color. A KOH solution consisting of 14 g of KOH in 100 cm³ of distilled water is then added slowly with constant stirring. Ammonium hydroxide is added until the solution just clears. The second AgNO₃ solution is added until a thin straw or brown precipitate appears. The solution is then filtered through glass wool. A dextrose solution consisting of 7.8 g of dextrose in 120 cm³ of distilled water is then mixed in and the particulate material to be plated is immediately immersed therein and left until coated with silver. To ensure that all surfaces of the particulates are plated, it is desirable that they be continuously stirred during the plating process.

The siliceous particulate substrate may range from essentially pure silica sand to a wide variety of calcined diatomaceous earths. The primary requirement of such substrates is that when silvered they present large effective surface areas for mercury collection. The literature reveals a wide variety of siliceous materials and calcined diatomaceous earths having surface areas ranging from about 0.6 to about 13 m²/g. When silvered, particulate siliceous substrates having effective surface areas in this range are suitable for use as amalgamating material 2. A preferred amalgamating material 2 is a commercially available type of calcined diatomite sold under the tradename Chromosorb P by Johns-Manville sized to 30–60 mesh and plated with silver. Chromosorb P is prepared by calcining natural diatomite (Kieselguhr) at a temperature up to 1600°C. Because natural diatomite does not have a constant composition, there is some variation in the chemical composition of Chromosorb P. Thus, Blandenet and Robin, J. Gas Chromat., p. 225 (July 1964) and Palframan and Walker, Analyst, vol. 92, p. 71 (1967) indicate the following compositions.

|  | Blandenet et al. | Palframan et al. |
|---|---|---|
| $H_2O$ | 0.28 | 0.3 |
| $SiO_2$ | 89.2 | 90.6 |
| $Al_2O_3$ | 5.1 | 4.4 |
| $Fe_2O_3$ | 1.50 | 1.6 |
| $TiO_2$ | 0.30 | 0.2 |
| CaO | 0.90 | 0.6 |
| MgO | 1.00 | 0.6 |
| $Na_2O$ | 0.70 | |
| $K_2O$ | 0.55 | 1.0 |

Palframan et al. report the surface area of 60 to 80 mesh Chromosorb P as 4.0 m²/g based on a Johns-Manville technical bulletin. Blandenet et al. report specific surface areas ranging from 2.80 to 5.24 m²/g, depending on the measuring technique.

The purpose of adsorber material 3 is to selectively and quantitatively adsorb organic mercurial vapors, e.g., those of methyl mercury chloride, dimethyl mercury, ethyl mercury chloride, diethyl mercury, and diphenyl mercury, while permitting the free passage of metallic mercury vapor therethrough. Adsorber material 3 may be such as to temporarily detrain mercury vapor from the air passing therethrough but may not adsorb it. That is to say, adsorber 3 must be capable of readily releasing any such detrained mercury to mercury-free air or inert gas passed therethrough while at the same time quantitatively retaining all adsorbed organic mercurials.

Selective adsorption of organic mercurial vapors may be achieved through use of a carbon molecular sieve as adsorber material 3. Porous carbon blacks are suitable for this purpose with preferred materials for adsorber 3 being carbon blacks prepared by thermal degradation of chlorine-containing polymers of the type having the general formula $(C_2H_2Cl_2)_n$ according to the reaction $$(C_2H_2Cl_2)_n \xrightarrow{\Delta} 2n\ C + 2n\ HCl.$$

A particularly useful material for adsorber 3 is prepared by the thermal degradation of polyvinylidene chloride and is sold under the tradename of Carbosieve B by Supelco, Inc., Bellefonte, Pa. 16823. Carbosieve B is the same porous carbon black known as type B carbon molecular sieve. See, e.g., R. Kaiser, "Carbon Molecular Sieve," Chromatographia, vol. 3, p. 38 (1970). It is essentially pure carbon, having a carbon content of 99.998%. Its density is 0.226 g/cm³ and it has a surface area of approximately 1000 m²/g and a pore radius in the range of 10–12 angstroms.

In the sampling tube of FIG. 1, the carbon adsorber 3 is preferably placed next to intake 11 rather than the silvered siliceous material 2 because there is a tendency for the silvered material 2 to collect those mercurial molecules containing both an organic and an inorganic component as, e.g., $CH_3HgCl$. This in turn would result in a false indication as to the relative content of organic mercurial vapors and metallic mercury vapor when the collected mercury is desorbed and analyzed. By assuring that all the air being sampled first passes through an adsorber 3 which quantitatively and selectively adsorbs all organic mercurial vapors, this problem is avoided.

The efficacy of a particular adsorber for mercury vapor or organic mercurial vapors is readily determined through use of a parameter called "breakthrough time." This is the period that a specified flow of a given concentration of the vapor can continue before detectable traces of mercury exit from the sampling tube. Breakthrough times are dependent on the configuration of the sampling tube, i.e., length of sorbent section, packing, etc., the concentration and type of vapor passing through the adsorber material, and the flow rate of the vapor through the sampling tubes. Breakthrough times for various types of mercury vapors for 45–60 mesh Carbosieve B and 30–60 mesh silvered Chromosorb P are given in Table I. The conditions under which these breakthrough times were determined are as follows: temperature, 20°C; sampling rate, 0.5 l/min; sampling tube i.d., 4 mm; concentration, threshold limit value (Hg°, 0.1 mg/m³) (organic Hg, 0.01 mg/m³).

Table I

| Vapor | Carbosieve B (2 mm section) | Silvered Chromosorb P (5 mm section) |
|---|---|---|
| Hg (metallic) | < 5 sec | 13 h |
| $CH_3HgCl$ | > 24 h | > 1 hr |
| $C_2H_5HgCl$ | > 24 h | not determined |
| $(CH_3)_2Hg$ | > 24 h | < 30 sec |
| $(C_2H_5)_2Hg$ | > 24 h | < 30 sec |
| $(C_6H_5)_2Hg$ | > 24 h | < 30 sec |

Analysis of mercury collected by a three-stage sampling tube is performed in the following manner assuming the use of a membrane filter as particulate filter 13. The membrane filter is removed from the samples and digested in a Teflon decomposition vessel with nitric acid. Particulate mercury in the digested filter is reduced to metallic mercury vapor and is transferred into a tube containing a silver coated particulate substrate of the type herein disclosed. From this tube, the amount of particulate mercury collected by the filter is determined in the same manner as indicated below for the analysis of organic mercurial vapors and metallic mercury vapor.

Before analysis is commenced, the two-section sampling tube of FIG. 1 used for the adsorption of organic and metallic mercury is first conditioned after sampling by passing either pure air or pure nitrogen or other nonreactive gas through the tube to remove any metallic mercury which may have remained in adsorber 3. Normally, a flow of several minutes duration at the normal sampling flow rate is adequate for this purpose. Tube 1 is then broken at region 15 between plugs 5 and 6 and the mercury content of sections 14 and 16 is analyzed separately. Adsorber 3 in section 14 contains mercury collected as organic mercurial vapor, while material 2 in section 16 contains only mercury collected as metallic mercury vapor. Each section is analyzed by thermally desorbing the mercury through the adsorption cell of a flameless atomic absorption spectrophotometer. Absorption signals at the 2537 A Hg line are recorded by strip chart recorders. The recorder signals are compared to standard calibration curves covering the concentration range over which sampling is being conducted, and the concentration of the mercury in the tube section is calculated from the signals. The mercury concentration in micrograms per cubic meter at the sampling conditions is calculated for each type of mercury using the following formula:

$$\frac{\mu g \ Hg}{m^3} = \frac{\mu g \ Hg \ from \ curve}{sampling \ rate \ (m^3/h) \times sampling \ time \ (h)}$$

Figure 3:
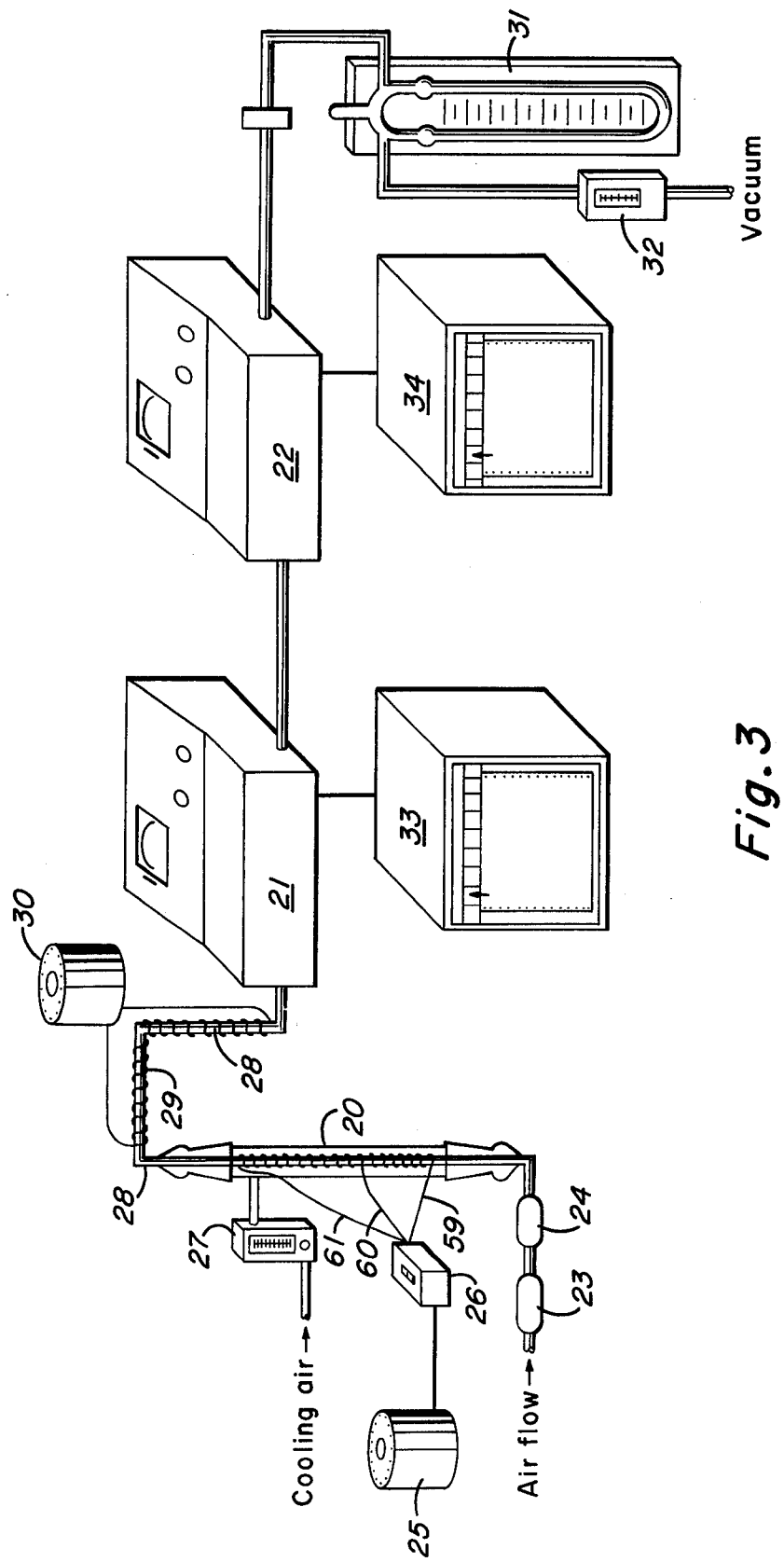
FIG. 3 is a schematic of an atmospheric mercury analysis system in accordance with the invention.

The mercury analysis system is shown schematically in FIG. 3. The primary components are thermal desorption unit 20 and flameless atomic absorption spectrophotometer 21 and 22. Section 16 of tube 1 containing metallic mercury vapor adsorber 2 or section 14 containing organic mercurial vapor adsorber 3 is placed in thermal desorption unit 20 and the air flow therethrough is adjusted to approximately 1.0 l/min. Air flow through the system is controlled by means of flowmeter 31 and rotometer 32. The air entering desorption unit 20 first passes through drying tube 23 containing a drying agent such as $Mg(ClO_4)_2$ and a filter 24 which removes any mercury that might be present in the air flow entering desorption unit 20. Preferably, filter 24 contains charcoal and silvered Chromosorb P. Air entering drying tube 23, filter 24 and desorption unit 20 is drawn from the surrounding ambient atmosphere by a vacuum pump (not shown). This pump is attached to a ballast tank to prevent fluctuations in air flow. In thermal desorption unit 20 either material 2 or adsorber 3 is heated to 700°C for a time sufficient to completely desorb all mercury therefrom. In the case of adsorber 3 for organic mercurials, the organic mercury compounds are reduced so that the mercury leaves unit 20 as metallic mercury vapor. Power for heating desorption unit 20 is provided by variable transformer 25 and transmitted to desorption unit 20 through three-way switch 26. Cooling air is metered into desorption unit 20 through flowmeter 27. The condensation of thermally desorbed mercury vapor in tube 28 is prevented by means of heating tape 29 powered by variable transformer 30.

Any reliable flameless atomic absorption spectrophotometer or mercury analysis system set to absorb the 2537 A wavelength of mercury may be used to detect the mercury vapor released from desorption unit 20. In FIG. 3, a dual optical cell system made from two modified Coleman Mercury Analyzer Systems (MAS-50) is shown. The modification consisted of changing the tubing in each MAS-50 to glass and rerouting to bypass the air pump. The air pump for each MAS-50 was turned off and not used. The reason for the use of two spectrophotometers is merely to extend the range of the method through the use of a dual optical cell system. Thus, spectrophotometer 21 has an absorption cell 15.5 cm in length and is used for the determination of mercury concentrations in the 0.001 to 0.20 $\mu g$ range. Spectrophotometer 22 has an absorption cell 2.5 cm long and is used for the determination of mercury concentration in the 0.01 to 2.5 $\mu g$ range. The range and sensitivity of the method is the same for the three forms of mercury, i.e., particulate, metallic vapor, and organic mercurial vapor, since the same analytical technique is used for each form. With modified Coleman Model MAS-50 spectrophotometers, the sensitivity of the method using the 0 to 100% absorption scale for both optical cells is 0.001 $\mu g$ for the 15.5 cm cell and 0.01 $\mu$ for the 2.5 cm cell. The range and sensitivity of the method may be extended, however, to as low as 0.002 $\mu g$ using electronic scale expansion. Absorption signals from the spectrophotometer 21 are recorded by 0–10 mV strip chart recorder 33 while those from spectrophotometer 22 are recorded by 0–10 mV strip chart recorder 34.

Figure 4:
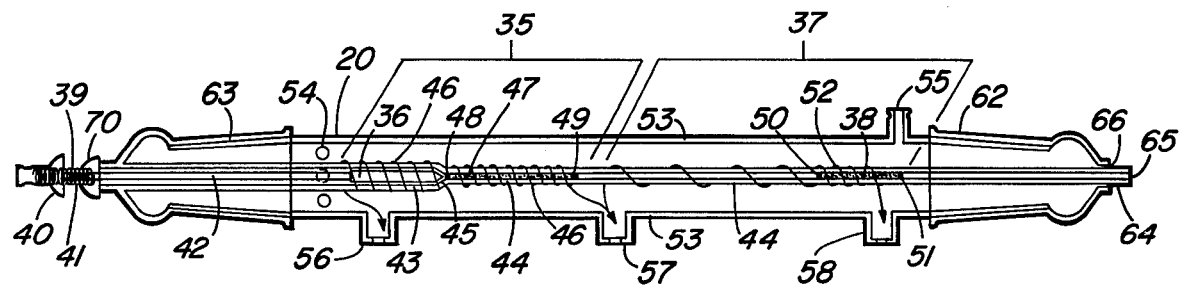
FIG. 4 is a cross-sectional view of a thermal mercury desorption unit useful in the practice of the invention.

Thermal desorption unit 20 is shown in more detail in FIG. 4. It is designed for the determination of mercury collected on 4 mm i.d. sampling tubes of the type shown in FIG. 1 and containing a silvered siliceous adsorber 2 and a high surface area carbon black adsorber 3. A sampling tube 36 is inserted into section 35 of desorption unit 20 where the mercury is thermally desorbed and transferred to section 37 which contains gold section 38. Gold section 38 contains gold granules which amalgamate all the mercury released from section 35 and allow impurities to pass. The mercury is then desorbed from granules 38 and passed into flameless atomic absorption spectrophotometers 21 and 22 (See FIG. 3) where the amount of desorbed mercury is determined. Sampling tube 36 is inserted into section 35 by means of loading mechanism 39. Mechanism 39 consists of a female glass joint 40, male glass joint 70, a steel spring 41, and a plunger tube 42. Tube 42 which may be 3 or 4 mm o.d. quartz glass has a length sufficient to hold sampling tube 36 lightly in place in desorption section 35 when spring 41 is appropriately adjusted. After sampling tube 36 is inserted, joints 40 and 70 are firmly mated by means of a clamp (not shown). Sample desorption section 35 is composed of 8 mm i.d. quartz tubing 43 and 5 mm i.d. quartz tubing 44 having a tapered junction 45 so that sampling tube tips fit snugly against the junction. Sample desorption section 35 is heated by 28 coils of 18-gauge Nichrome wire 46 wrapped around tubes 43 and 44. Just downstream of taper 45, tube 44 contains a 40 mm section of rod-shaped CuO 47 held in place by quartz glass wool plugs 48 and 49. When heated, CuO 47 oxidizes organic vapors desorbed from the sampling tube. Section 37 which contains gold section 38 is an extension of tube 44. Desorption section 37 has 30 coils of size 20 Nichrome wire 52 wrapped around tube 44 with the coils concentrated over gold section 38. Gold section 38 consists of a 25 mm length of 35–50 mesh granular gold mixed one-to-one with 20–40 mesh sea sand. The sand is added to the gold to prevent fusing of the gold and to allow better air flow therethrough. The mixture of gold and sand is held in place by quartz glass wool plugs 50 and 51. Surrounding desorption sections 35 and 37 is cooling jacket 53 made of Pyrex glass. Jacket 53 not only contains the flow of cooling air but also acts as electrical insulation for heating coils 46 and 52. Cooling air enters jacket 53 through intake 55 and exits through a plurality of vents 54 spaced around jacket 53. In the embodiment shown in FIG. 4, there are seven vents 54. Leads 59, 60, and 61 for heating coils 46 and 52 from three-way switch 26 (see FIG. 3) enter jacket 53 through 5 mm holes in glass nipples 56, 57, and 58, respectively. Solderless connectors (not shown) between leads 59, 60, and 61 and coils 46 and 52 are placed inside jacket 53 to prevent exposing uninsulated wire outside jacket 53. Insulated leads 59, 60, and 61 are sealed in place with a heat resistant sealer. Jacket 53 is tapered somewhat at both ends and mated to end closures 62 and 63. Outlet 64 from desorption unit 20 is butt connected with a Tygon overseal to glass tube 28 (see FIG. 3) which leads to spectrophotometer 21. To make this connection the end 65 of quartz tube 44 slides through opening 66 in closure 62. Opening 66 is kept to a minimum to limit the escape of cooling air from jacket 53.

Operation of the analysis system shown in FIGS. 3 and 4 is straightforward. Spectrophotometers 21 and 22 are turned on and allowed to stabilize as is heating tape 29. The vacuum pump is then turned on and flowmeter 31 used to adjust the flowrate through the system to about 1.0 l/min. The optimum flowrate may readily be determined by analyzing standards and determining which rate of flow gives optimum recorder responses. Cooling air flow through desorption unit 20 is commenced and the rate of flow adjusted to about 15 l/min by means of flowmeter 27. Recorders 33 and 34 are turned on and allowed to stabilize. Spectrophotometers 21 and 22 and recorders 33 and 34 are then adjusted to the desired 0 and 100% transmittance settings. The system is purged by switching three-way switch 26 to heat desorption section 35 of desorption unit 20 for 30 seconds and then switching immediately to heat section 37 for 30 seconds.

After the desorption unit 20 is allowed to cool for one minute, analysis commences by removing the clamp from joints 40 and 70, inserting sampling tube 36 which contains either amalgamating material 2 or adsorber 3, reclamping joints 40 and 70, switching on the heat section 35 of desorption unit 20 for 30 seconds, and then immediately switching to heat section 37 for about 25 seconds. At this time recorder 33 and 34 will record the absorption signal of any mercury desorbed from sampling tube 36. Three-way switch 26 is then turned to its off position, desorption unit 20 allowed to cool, and sample tube 36 is removed. The cycle is then repeated with a new sample tube.

The foregoing description and examples are illustrative only and the scope of the invention is not limited to the embodiments described herein.

What we claim is:

1. A sampling tube for simultaneously and selectively sampling organic and metallic mercury vapors from air which comprises (a) a cylinder having an air intake end and an air outlet end, (b) a first particulate adsorber within said cylinder and adjacent said air intake end for selectively and quantitatively adsorbing organic mercurial vapors in air passing therethrough, (c) a second particulate adsorber within said cylinder for adsorbing metallic mercury in air passing therethrough, and (d) porous plug means for maintaining said first and second adsorbers in spaced relationship in said cylinder, said plug means producing no substantial pressure drop in air passing through said cylinder.

2. The sampling tube of claim 1 having spacer means intermediate said plug means for maintaining said first and second adsorbers in spaced relationship within said cylinder.

3. The sampling tube of claim 1 wherein said first adsorber is carbon black consisting essentially of pure carbon having a surface area of about 1000 m²/g and a pore radius of 10 to 12 angstroms, and said second absorbing material is a silvered calcined diatomaceous earth.

4. The sampling tube of claim 1 having filter means for removing and collecting particulate mercury from air entering the intake end of said cylinder.

5. A method for determining the content of mercury in organic mercurial and metallic mercury vapors in air which comprises (a) passing a known volume of said air through a first adsorber which selectively and quantitatively adsorbs organic mercurial vapors, (b) then passing said air volume through a second adsorber which quantitatively adsorbs metallic mercury vapor, (c) individually thermally desorbing collected vapors from said first and second adsorbers, (d) reducing said desorbed organic mercurial vapors to metallic mercury vapor, and (e) individually measuring by flameless atomic adsorption spectroscopy the amount of metallic mercury vapor obtained from each of said first and second adsorbers.

6. The method of claim 5 wherein after said known volume of air has passed through said first and second adsorbers pure air or inert gas is passed through said first and second adsorbers for a time sufficient to detrain any metallic mercury vapor in said first adsorber and adsorb it in said second adsorber.

* * * * *